US012667481B2

(12) United States Patent
Tao et al.

(10) Patent No.: US 12,667,481 B2
(45) Date of Patent: Jun. 30, 2026

(54) HEAT TRANSFER DEVICE AND SYSTEM

(71) Applicant: THE HONG KONG POLYTECHNIC UNIVERSITY, Hong Kong (CN)

(72) Inventors: Xiaoming Tao, Hong Kong (CN); Ying Xiong, Hong Kong (CN); Shengyang Tang, Hong Kong (CN); Jing Yang, Hong Kong (CN); Mingyue Zhu, Hong Kong (CN)

(73) Assignee: The Hong Kong Polytechnic University, Hong Kong (CN)

( * ) Notice: Subject to any disclaimer, the term of this patent is extended or adjusted under 35 U.S.C. 154(b) by 287 days.

(21) Appl. No.: 18/466,874

(22) Filed: Sep. 14, 2023

(65) Prior Publication Data

US 2025/0090370 A1     Mar. 20, 2025

(51) Int. Cl.
*A61F 7/02*          (2006.01)
*A61F 7/00*          (2006.01)

(52) U.S. Cl.
CPC ........ *A61F 7/02* (2013.01); *A61F 2007/0039* (2013.01); *A61F 2007/0054* (2013.01); *A61F 2007/0228* (2013.01); *A61F 2007/0244* (2013.01)

(58) Field of Classification Search
CPC ................ A61F 7/02; A61F 2007/0039; A61F 2007/0054; A61F 2007/0228; A61F 2007/0244; A61F 2007/0042; A61F 2007/0233; A41D 13/0053
USPC ....................................................... 607/104
See application file for complete search history.

(56) References Cited

U.S. PATENT DOCUMENTS

| | | | | |
|---|---|---|---|---|
| 4,149,541 A * | 4/1979 | Gammons | ................. | A61F 7/02 |
| | | | | 607/104 |
| 6,551,347 B1 * | 4/2003 | Elkins | ........................ | A61F 7/02 |
| | | | | 607/104 |
| 6,695,872 B2 | 2/2004 | Elkins | | |
| 7,198,093 B1 | 4/2007 | Elkins | | |
| 7,896,910 B2 | 3/2011 | Schirrmacher et al. | | |
| 9,192,539 B2 | 11/2015 | Parish et al. | | |
| 9,943,437 B2 | 4/2018 | Lowe et al. | | |
| 11,547,625 B2 * | 1/2023 | Lowe | .................. | A61H 9/0092 |
| 2001/0034545 A1 * | 10/2001 | Elkins | ....................... | A61F 7/02 |
| | | | | 607/108 |

(Continued)

FOREIGN PATENT DOCUMENTS

| | | | | | |
|---|---|---|---|---|---|
| WO | WO-2005007060 A2 * | 1/2005 | ............... | A61F 7/02 | |
| WO | WO-2019139593 A1 * | 7/2019 | ........... | A61N 5/0624 | |

(Continued)

*Primary Examiner* — Beverly M Flanagan
(74) *Attorney, Agent, or Firm* — S&F/WEHRW

(57) ABSTRACT

A heat transfer device for applying a varying temperature to a portion of an animate body comprises a liquid conduit. The liquid conduit is liquidly connectable to an external first liquid source to establish a first circulation loop for transporting a first liquid. The liquid conduit is liquidly connectable to an external second liquid source to establish a second circulation loop for transporting a second liquid. The second liquid has a higher temperature than the first liquid. The liquid conduit is operably switchable between the first circulation loop and the second circulation loop for achieving the varying temperature applied to the portion of the animate body.

16 Claims, 11 Drawing Sheets

(56) References Cited

U.S. PATENT DOCUMENTS

| | | | | |
|---|---|---|---|---|
| 2012/0191035 A1* | 7/2012 | Stephan | ................. | A61F 7/007 |
| | | | | 604/23 |
| 2020/0000628 A1* | 1/2020 | Lowe | ....................... | A61F 7/00 |

FOREIGN PATENT DOCUMENTS

| | | | | | |
|---|---|---|---|---|---|
| WO | WO-2021184872 A1 * | 9/2021 | ....... | B29C 66/81411 |
| WO | WO-2022272067 A1 * | 12/2022 | ........... | A61H 9/0078 |

* cited by examiner

10

120-1

121a 120-1

121b 120-2

120-3

HEAT TRANSFER DEVICE AND SYSTEM

FIELD OF THE INVENTION

The present disclosure generally relates to animate body heat exchange, and more particularly to heat transfer device and system for animate body heat exchange.

BACKGROUND

Rapid contrast temperature therapy (RCT) with immersion into hot and cold fluid alternatively has been validated as an effective approach for improving conditions of animate body, such as improving functionality for a certain portion of human body, such as legs, arms, elbows, etc. For example, RCT can help recovery of post-exercise muscle fatigue and soreness. For another example, cyclic RCT can effectively help reduce unwanted edema, soreness and muscle damage, increase blood flow and heat, and promote metabolism and relaxation of tissues after high-intensive exercise. In addition to rest, ice assisted, compression therapy, RCT has gradually become one preferred physical recovery strategy for elite athletes. Wearable RCT devices are more desirable than the water immersion RCT because of the convenience, personal hygiene and space limitation. The existing systems for RCT have disadvantages in various aspects, such as unsatisfactory efficacy, limited applications, etc.

It is an object of the present disclosure to overcome or substantially ameliorate one or more of the disadvantages of prior art, or at least to provide a useful alternative.

SUMMARY

In one aspect of the present disclosure there is provided a heat transfer device for applying a varying temperature to a portion of an animate body. The heat transfer device comprises a liquid conduit. The liquid conduit is liquidly connectable to an external first liquid source to establish a first circulation loop for transporting a first liquid. The liquid conduit is liquidly connectable to an external second liquid source to establish a second circulation loop for transporting a second liquid. The second liquid has a higher temperature than the first liquid. The liquid conduit is operably switchable between the first circulation loop and the second circulation loop for achieving the varying temperature applied to the portion of the animate body.

In another aspect of the present disclosure there is provided a heat transfer system. The heat transfer system comprises a wearable apparatus and a portable apparatus. The wearable apparatus is configured to be wearable on a portion of an animate body for applying a varying temperature to the portion of the animate body. The wearable apparatus comprises a heat transfer device. The portable apparatus is connectable to the wearable apparatus for supplying liquid with the varying temperature to the wearable apparatus. The portable apparatus comprises a first liquid source, a second liquid source, and a control unit, wherein the heat transfer device comprises a liquid conduit. The liquid conduit is liquidly connectable to the first liquid source to establish a first circulation loop for carrying a first liquid. The liquid conduit is liquidly connectable to the second liquid source to establish a second circulation loop for carrying a second liquid, the second liquid has a higher temperature than the first liquid. The control unit is configured to switch connection of the liquid conduit between the first circulation loop and the second circulation loop for achieving the varying temperature applied to the portion of the animate body.

Other example embodiments are discussed herein.

BRIEF DESCRIPTION OF THE DRAWINGS

Embodiments of the invention will now be described, by way of example only, with reference to the accompanying drawings in which.

DETAILED DESCRIPTION

Figure 1:
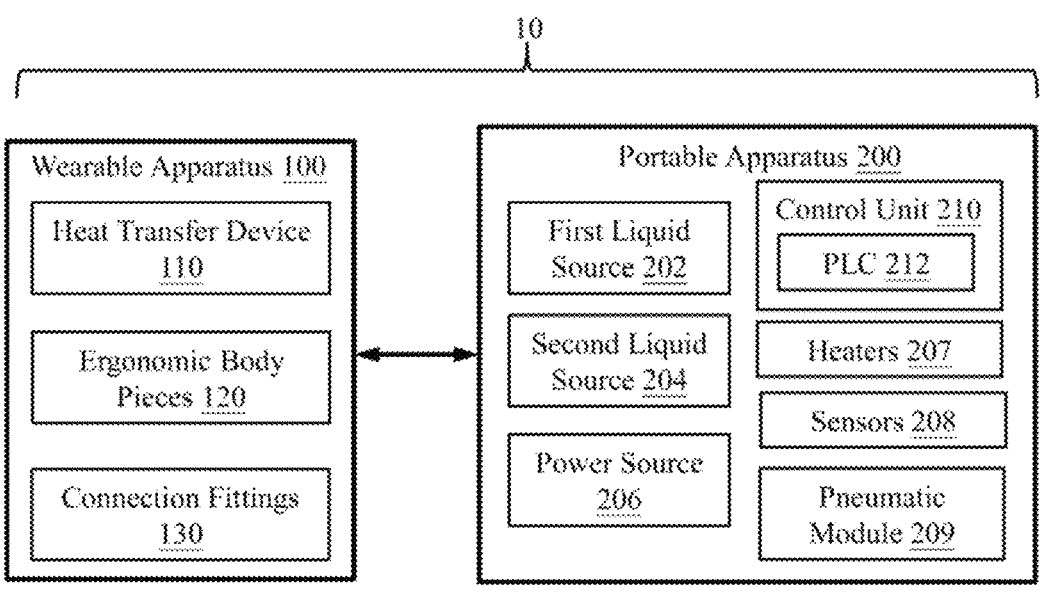
FIG. 1 illustrates a heat transfer system according to certain embodiments of the present disclosure.

The present disclosure will now be described with reference to the following examples which should be considered in all respects as illustrative and non-restrictive. In the Figures, corresponding features within the same embodiment or common to different embodiments have been given the same or similar reference numerals.

Throughout the description and the claims, the words "comprise", "comprising", and the like are to be construed in an inclusive sense as opposed to an exclusive or exhaustive sense; that is to say, in the sense of "including, but not limited to".

Furthermore, as used herein and unless otherwise specified, the use of the ordinal adjectives "first", "second", etc., to describe a common object, merely indicate that different instances of like objects are being referred to, and are not intended to imply that the objects so described must be in a given sequence, either temporally, spatially, in ranking, or in any other manner.

Example embodiments relate to heat transfer device and system with novel design and improved performance.

Many existing RCT technologies are flawed in various aspects. For example, a sharp temperature contrast per unit of time is generally desirable as it improves efficacy for the therapy. However, the existing systems are unsatisfactory in achieving a sharp temperature contrast in a short time. Furthermore, there are significant variations for temperature distribution for some RCT devices, which adversely affects the effectiveness of heat exchange with the animate body. Also, some RCT devices are powered through electrical ports that interface with a mainline electric power supply. They are generally too bulky and heavy and therefore are limited to in-door applications rather than on-field usage. Moreover, many existing portable technologies can deliver only a single treatment, either hot or cool treatment, in alternative series as required by RCT. Usually physiotherapists have to apply cold plus compression therapy on field as the main outdoor physical recovery strategy. This, however, has less efficacy. As another example, many existing systems use semiconductor thermoelectric modules to provide hot and cold sources. However, they have a low energy conversion ratio for the cold sources, and therefore more energy would be consumed.

Example embodiments solve one or more of these problems associated with the existing systems and provide technical solutions with novel designs. Specifically, example embodiments provide heat transfer device and system for applying a varying temperature to a portion of an animate body with improved performance. The heat transfer device and system may be employed in various industrial applications.

For a RCT device or system, a fast switching between high and low temperatures is desirable. The present inventors have recognized that by carefully designing a circulation architecture comprising two liquid circulation loops, one comprising a first liquid source with a low temperature (such as a cold tank receiving icy water) and the other comprising a second liquid source with a high temperature (such as a hot tank with heated water at a degree of 20° C., 30° C., 40° C., etc.), such that the heat transfer device is switchable between the two circulation loops, the switching time between high and low temperatures applied to a portion of an animate body can be reduced, thereby bettering the treatment on the animate body.

The present inventors have further recognized the benefits of providing a branch such that one end of the branch connects to the inlet of the heat transfer device and the other end of the branch connects to the outlet of the heat transfer device, where the branch comprises a valve to control opening or closing of the branch. In this way, during the temperature switching, the residual or leftover liquid in the heat transfer device can be quickly drained out and into the respective liquid source. For example, the residual or leftover cold liquid can be drained out of the loop and into the cold tank quickly before and/or when circulation of the hot liquid starts. The residual or leftover hot liquid can be drained out of the loop and into the hot tank quickly before and/or when circulation of the cold liquid starts. As such, the switching time between high and low temperatures applied to the animate body can be further reduced.

According to some embodiments, the temperature applied to the animate body can be switched between 5° C. and 40° C. within 10 seconds(s) (i.e., the switching time is 10 s and the switching speed is around 3.5° C. per second). This temperature range covers commonly used range for RCT. Further, as far as the knowledge of the present inventors, this switching time is smaller than that for the existing systems. It is noted that the 10 s of switching time for the temperature range between 5° C. and 40° C. is a target set by sports institute, and no existing system has achieved this target before the present disclosure. That is, the system according to one or more embodiments of the present disclosure achieves fastest RCT switching speed. The reduced switching time or increased switching speed improves the effectiveness of treatment by RCT on the animate body. Therefore, the device and system according to the present disclosure have a wider range of applications with improved performance.

According to one or more embodiments, the present inventors have recognized that by carefully designing the structure of the heat transfer device, the temperature can be quickly and evenly distributed across the liquid conduit of the heat transfer device. For example, as described later below, the heat transfer device comprises line connections and dot connections, and the active area of the heat transfer device can be divided into four areas or regions. The four areas comprise a first area, a second area, a third area, and a fourth area such that substantial proportion of the liquid flow subsequently through the first area, the second area, the third area, and the fourth area. The flowing of the liquid and the temperature distribution will be improved when the dot connections of the fourth area have larger density than the dot connections in the first area. For example, according to some embodiments, a numeral analysis (such as from the infrared thermal imaging photos) shows around 80% of the active area reaches the required or desirable temperature within 10 s.

Further, the heat transfer system according to one or more embodiments consumers less energy compared to the existing systems. For example, (24V, 30 A) of power is sufficient for the heat transfer system (that is, the actual power needed is around 600 W). Therefore, one or more batteries, such as rechargeable batteries, can be used to power the system. As such, the heat transfer system according to one or more embodiments can be used in a wider range of applications, such as outdoors, where the mainline electric power supply may be unavailable.

FIG. 1 illustrates a heat transfer system 10 according to certain embodiments of the present disclosure. The heat transfer system 10 is wearable on a portion of an animate body such that the portion can be treated with an applied varying temperature. The animated body may be a body of a living human or animal. The portion may be a leg, an arm, an elbow, etc. or one or more parts therefor.

The heat transfer system 10 comprises a wearable apparatus 100 and a portable apparatus 200. The wearable apparatus 100 can be worn onto the portion of the animate body, or attached to the portion in a proper manner. For example, the wearable apparatus 100 may be wrapped around a person's leg or arm. The portable apparatus 200 provides fluid, such as liquid, with a predetermined temperature to the wearable apparatus 100 such that the temperature, through the fluid as a heat exchange medium, can be applied to the portion of the animate body for activating or treating the portion or providing certain favourable assistance to the portion, such as helping the portion function better.

The wearable apparatus 100 comprises a heat transfer device 110. The portable apparatus 200 comprises a first liquid source 202, a second liquid source 204, and a control unit 210. The heat transfer device 110 comprises a liquid conduit. The liquid conduit is liquidly connectable to the first liquid source 202 to establish a first circulation loop for carrying a first liquid. The liquid conduit is liquidly connectable to the second liquid source 204 to establish a second circulation loop for carrying a second liquid. The second liquid has a higher temperature than the first liquid. The control unit 210 is configured to switch connection of the liquid conduit between the first circulation loop and the second circulation loop for achieving the varying temperature applied to the portion of the animate body.

The first and second liquid may be water, oil, or other proper liquid (such as coolant, or certain liquid with high specific heat capacity) as long as it can act as a heat exchange medium carrying a desirable temperature for purpose of the present disclosure. In some embodiments, the first liquid source 202 is a cold tank and the first liquid is a mixture of water and coolant. The coolant may be ice. In some embodiments, the second liquid source 204 is a hot tank and the second liquid may be heated water. For example, the second liquid source 204 may be heated by heaters 207 to generate the heated water.

The control unit 210 may comprise pumps and valves that form a part of the first circulation loop and/or the second circulation loop. The control unit 210 may comprise a programmable logic controller (PLC) 212 that controls opening or closing of one or more of the pumps and valves, as exemplified later below. The PLC 212 is programmable to vary the control logic such that operation of the system 10 can be personalized. For example, the PLC 212 can be programmed to set sequential logic, thereby to predetermine the switching time, the operation modes, etc. In some embodiments, the PLC 212 can be programmed to set a hot and cold fast switching mode, a cold mode, a hot mode, and a compression mode. The temperature range may be set from 3-45° C. and the total time of operation of the system 10 may be set as 10-20 min. For a RCT treatment, the time for each of the cold and hot temperatures may be set individually as 1-2 min, the number of cycles may be set as 3-5 times and the quick changeover may be set as short as 10 s.

The portable apparatus 200 may comprises sensors 208 to monitor the temperature of the first liquid and/or second liquid. The obtained temperature may be fed into one or more thermal feedback loops, thereby to stabilize the temperature in the first liquid source 202 and/or second liquid source 204.

The portable apparatus 200 may comprises a power source 206 for supplying power to the heat transfer system 10, such as to power various electronics disposed within the system 10. The power source 206 may comprise an interface that is electrically connectable to a mainline electric power supply. Alternatively and advantageously, the power source 206 may comprise one or more batteries, such as rechargeable batteries, such that the system 10 can be conveniently used where the mainline electric power supply is not accessible, such as outdoors.

The portable apparatus 200 may comprise a pneumatic module 209 for providing pressured gas to the gas conduit in the heat transfer device 110, thereby to provide compression against the portion of the animate body. In some embodiments, the pneumatic module 209 comprises one or more air pumps and valves. The pneumatic module 209 discharges pressurized air into the gas conduit, thereby to push the liquid conduit against the portion of the animate body. This facilitates the heat exchange between the liquid in the heat transfer device 110 and the animate body because the liquid conduit is pushed closer to the portion of the animate body, thereby to improve the effectiveness and efficiency of RCT. In some embodiments, under certain operation mode, the pneumatic module 209 discharges pressurized air into the gas conduit at a certain frequency or at a varying frequency, thereby to massage the animate body. In some embodiments, the pneumatic module comprises an air pump and an electrical proportional valve. In operation, the air pump supplies air to the gas conduit of the heat transfer device such that the gas conduit (and accordingly the heat transfer device) is expanded to apply compression. By controlling the voltage, the electrical proportional valve can control the volume of air and thus the amount of pressure. Varying pressures can create a massage effect. Provision of the pneumatic module is advantageous in certain applications where the massage helps treatment or activation on the animate body.

The wearable apparatus 100 may comprise ergonomic body pieces 120 for carrying or housing the heat transfer device 110. For example, the ergonomic body pieces 120 may have a similar shape and configuration as the heat transfer device 110 such that when the heat transfer device 110 is received within the inner space of the ergonomic body pieces 120, they can be closely matched and coupled to reduce the gap therebetween, thereby not to adversely affect the heat exchange between the heat transfer device 110 and the animate body. The ergonomic body pieces 120 can adopt ergonomic design so as to be compatible and conformable to the animate body. The ergonomic body pieces 120 may comprise fixtures for fixing the ergonomic body pieces 120 to the animate body when the ergonomic body pieces 120 are attached to the portion of the animate body. The fixtures may comprise a plurality of buckles and a plurality of straps. In some embodiments, each strap may have a hook for connecting to a corresponding buckle. In some other embodiments, each strap may have an adhesive tab such that it can be fixed onto the strap after passing through the buckle.

The wearable apparatus 100 may comprise connection fittings 130. The connection fittings 130 may comprises plural tubes (such as two pairs of tubes or three pairs of tubes) for connecting the heat transfer device 110 to the portable apparatus 200. Fluid, such as liquid, can be delivered from the portable apparatus 200 to the heat transfer device 110 and back to the portable apparatus 200 via the tubes. The tubes may be designed to connect one or more heat transfer devices 110 at the same time. To improve durability, each tube may be covered with an insulating material and a protective sleeve. The tubes may be provided with one or more reinforcement features between the portable apparatus 200 and the heat transfer device 110 to prevent the tubes from falling out.

The portable apparatus 200 may be a modular or all-in-one apparatus such that it saves space, consumes less energy, and is easy to assembly and transport. The portable apparatus 200 may be customized according to scenarios where it is applied.

Figure 2:
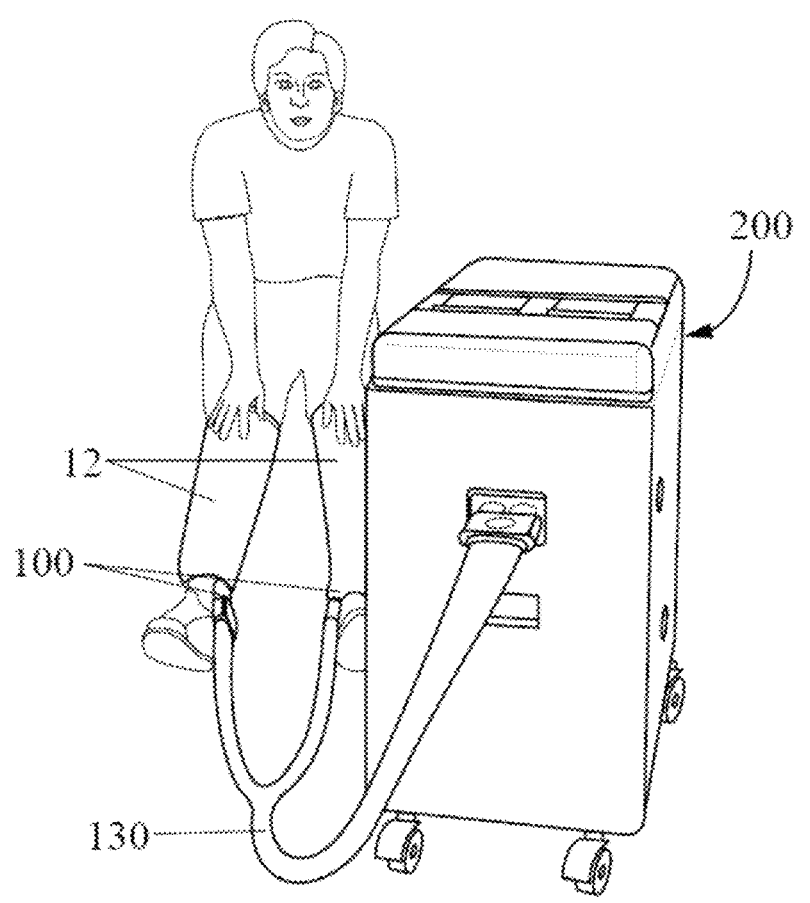
FIG. 2 illustrates application of temperature by a heat transfer system to a person's legs according to certain embodiments of the present disclosure.

FIG. 2 illustrates a heat transfer system applied to a person's legs 12 for RCT treatment. The heat transfer system comprises two wearable apparatus 100 and a portable apparatus 200. Each wearable apparatus 100 is connectable to the portable apparatus 200 via connection fittings 130 and wrapped onto a respective leg for heat exchange with that leg. The control unit of the portable apparatus 200 can be programable to control how the two wearable apparatus 100 operate. For example, the two wearable apparatus 100 may operate simultaneously, or in a predetermined sequence.

Figure 3:
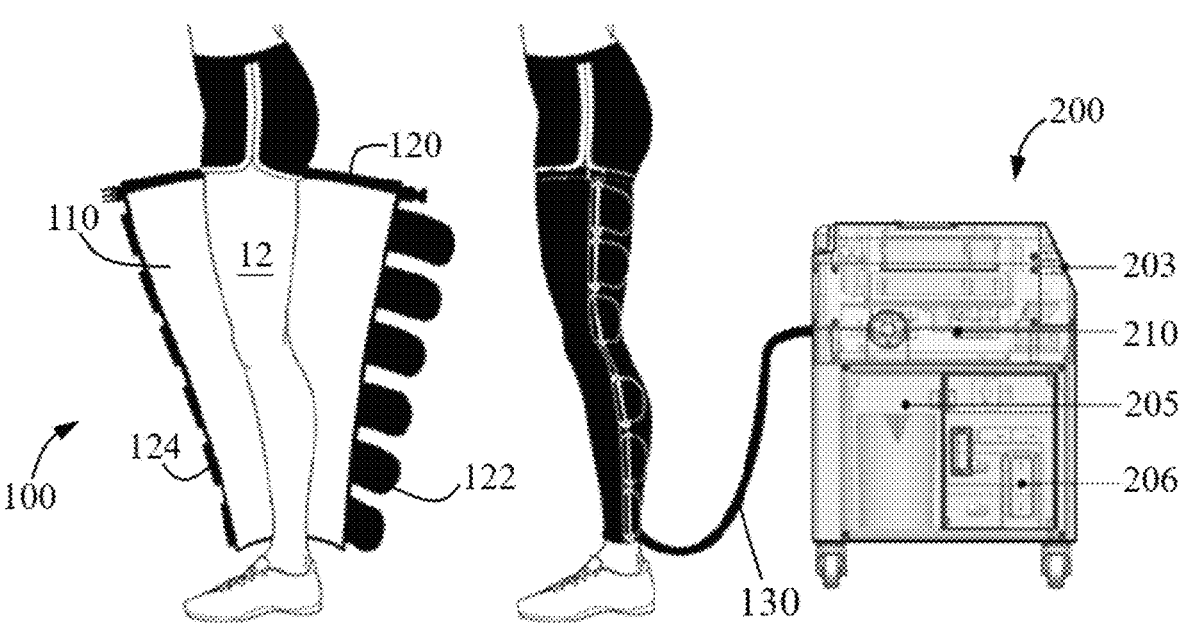
FIG. 3 illustrates architecture of a heat transfer system applied to a person's leg according to certain embodiments of the present disclosure.

Referring to FIG. 3, the heat transfer device 110 of the wearable apparatus 100 is carried by the ergonomic body pieces 120. When conducting the RCT treatment, the ergonomic body pieces 120 and the heat transfer device 110 together wrap around the person's leg 12. The ergonomic body pieces 120 comprise straps 122 and buckles 124 for fixing the wearable apparatus 100 onto the leg 12, thereby to ensure a desirable contact between the ergonomic body pieces 120 and the leg 12 for favourable heat transfer. The connection fittings 130 connect the heat transfer device 110 to the portable apparatus 200. In some embodiments, the connection fittings 130 may be considered as part of the portable apparatus 200.

The portable apparatus 200 is provided with a communication unit 203 and an accessory storage 205. The communication unit 203 comprises network interface and/or user interface and various software that enables automation or operation of the system. The communication unit 203 may be considered as part of the control unit 210. The accessory storage 205 provides space for receiving various components. For example, the connection fittings 130 may be stored in the accessory storage 205 when the system is not in use. The accessory storage 205 may also provide space for users' customization, such as addition of one or more features. The power source 206 may comprise an interface, such as a plug, that is electrically connectable to a main mainline electric power supply, or one or more rechargeable batteries, or both.

Figure 4:
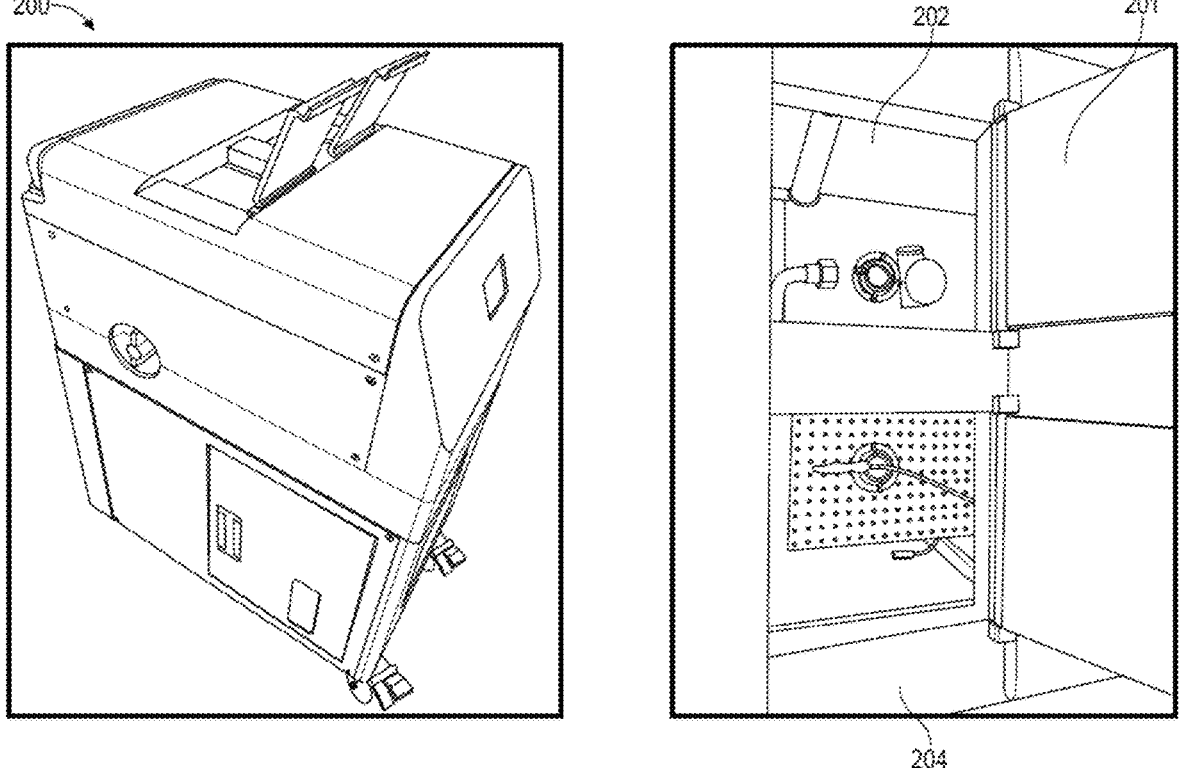
FIG. 4 illustrates a prototype for a portable apparatus of a heat transfer system according to certain embodiments of the present disclosure.

FIG. 4 shows a prototype of the portable apparatus 200. The door 201 is opened such that the first liquid source 202 and the second liquid source 204 are viewable. The prototype is only an illustrative example, and it will be appreciated that the portable apparatus 200 can be structurally configured differently as long as it can fulfill the functions as described herein in accordance with one or more embodiments.

Figure 5:
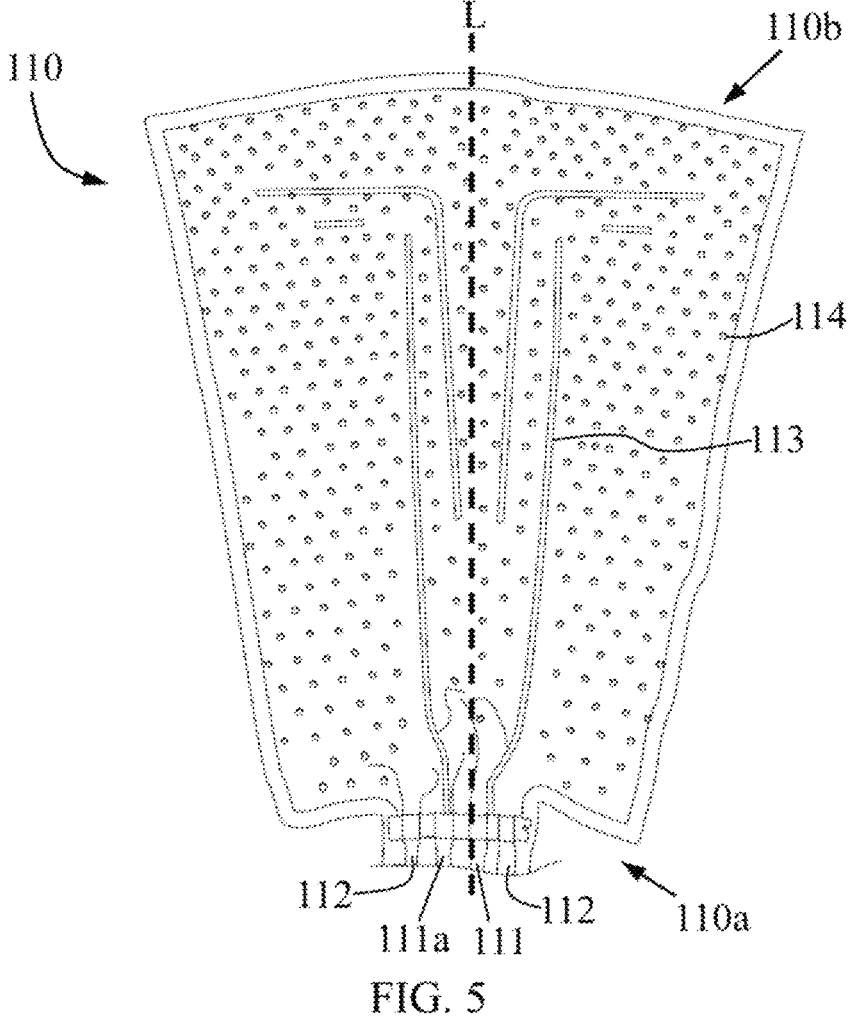
FIG. 5 illustrates a heat transfer device according to certain embodiments of the present disclosure.

FIG. 5 illustrates a top view of a heat transfer device 110. The heat transfer device 110 has a first end 110a and a second end 110b opposite the first end 110a. A longitudinal line L extends from the first end 110a towards the second end 110b. In some embodiments, the heat transfer device 110 may be symmetrical relative to the longitudinal line L.

The heat transfer device 110 may comprise two or more layers that define a liquid conduit therein. As used herein, a liquid conduit may comprise one or more conduits, which, for convenience of description, may be collectively called a liquid conduit. The layers may be formed from separate pieces that are connected (such as welded) at their borders or edges to form a confined space for liquid flowing therein. Alternatively, the layers may be formed from a single piece that is subject to a proper processing (such as folded and welded at the folded lines) to form a confined space for liquid flowing therein.

The heat transfer device 110 has an inlet 111 for receiving liquid and two outlets 112 for discharging liquid. In the present embodiment, both the inlet 111 and the two outlets 112 are disposed at the first end 110a. This is advantageous as the liquid can be fully circulate within the liquid conduit to distribute heat evenly for purpose of treating on the animate body. This also improves the efficiency of heat transfer as more heat will be utilized for purpose of RCT treatment.

The inlet 111 may comprise one or more ports connectable to one or more liquid sources via connection fittings. For example, the inlet 111 may comprises a short pipe that is able to connect to a first liquid source or a second liquid source through the connection fittings for receiving liquid from the respective liquid source. The outlets 112 may comprises ports that are able to connect to a first liquid source and/or a second liquid source through the connection fittings for discharging liquid into the respective liquid source.

In some embodiments, the heat transfer device 110 has a gas conduit for receiving gas, such as air. As used herein, a gas conduit may comprise one or more conduits, which, for convenience of description, may be collectively called a gas conduit. Accordingly, the heat transfer device 110 is provided with a gas inlet 111a for receiving gas. The gas inlet 111a is connectable to one or more gas source via the connection fittings, where in such scenarios, the connecting fittings comprise a tube specifically for gas transportation.

Further, the heat transfer device 110 comprises line connections 113 and dot connections 114 for modifying the liquid conduit. For purpose of clarity and simplicity, only one dot connection and one line connection are referenced with signs in FIG. 5. Take an example where the heat transfer device 110 comprises a top layer and a bottom layer that define the liquid conduit. The line connections 113 and dot connections 114 provide coupling lines and dots for the two layers. As a result, the liquid is blocked by and cannot pass through the line connections 113 and dot connections 114. That is, the liquid conduit is modified or changed by the line connections 113 and dot connections 114 such that flowing of liquid therein is modified or constrained. As demonstrated later below, by carefully configuring the line connections 113 and dot connections 114, such as their location, density, size, shape, etc, an improved distribution of temperature within the heat transfer device 110 can be achieved.

The line connections 113 and dot connections 114 can be formed by proper process. For example, they can be formed by welding process, such as high-frequency welding, for bonding the top and bottom layers. It is further noted that when the heat transfer device comprises a gas conduit, the line connections and dot connections also modify the gas conduit for guiding the gas flowing therein.

Figure 6:
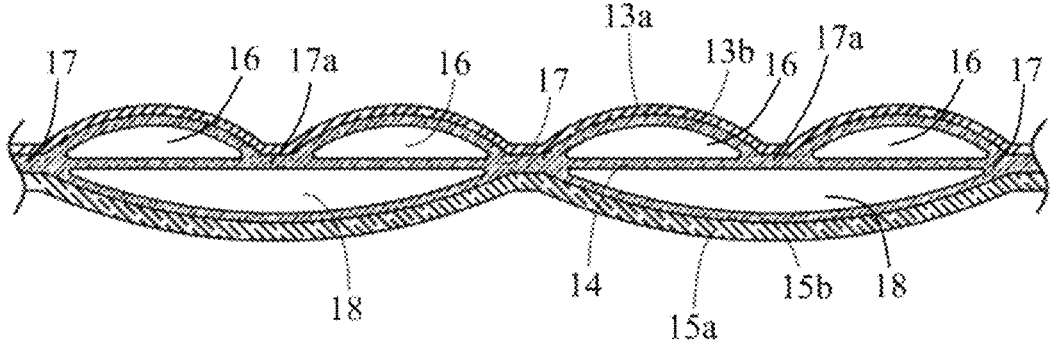
FIG. 6 illustrates a cross-sectional view of a part of a heat transfer device according to certain embodiments of the present disclosure.

FIG. 6 illustrates a cross-sectional view of a small portion of a heat transfer device. The heat transfer device 110 comprises a first layer and a second layer that form the liquid conduit. The first layer is operably disposed closer to the portion of the animate body than the second layer. The first layer has a smaller hardness than the second layer, but larger heat flux than the second layer.

The first and second layers may be fabricated with various thermoplastic adhesive films (TAFs) (e.g., thermoplastic polyurethane, polyvinylchloride, poly(ether sulfones), polyolefin) laminated fabric to form a liquid conduit. In the present embodiment, the first layer (also called inner layer) is TAF 13b laminated fabric 13a, where in operation, the fabric 13a is proximate to the surface (such as a skin) of the animate body. The second layer (also called middle layer) is a TAF film 14 or double TAF laminated fabrics 14. The first and second layers form a liquid conduit 16. The first and second layer may be bonded via dot connections 17, 17a via a high frequency welding.

In the present embodiment, the heat transfer device further comprises a third layer (also called outer layer) such that the second layer is disposed between the first layer and the third layer. The second layer and the third layer define a gas conduit 18 for receiving pressured gas for applying compression (such as massage therapy) to the portion of the animate body. The third layer may be a TAF 15b laminated fabric 15a.

The three layers may be fabricated in a same process to form the liquid conduit and gas conduit simultaneously. The three layers may be bonded together via high frequency welding, such that the three layers are melt and fused together at the dot connections 17.

Table 1 below shows exemplary parameters of materials, such as yarn counts, density, film thickness and fabric weight, used for fabricating the heat transfer device. Softer TAF laminated fabric is chosen as the inner layer as it is conformable to the skin surface and comfortable for users.

(Area III, also called a corner area), and a fourth area (Area IV, also called a main function area). Substantial proportion of the liquid flow subsequently through the first area, the second area, the third area, and the fourth area.

The present inventors have recognized that the configuration of the four areas has influence on the system performance, and can be designed to reduce the flow resistance and improve or maximize the kinetic energy contribution to heat convection. The liquid flow can be guided along the longitudinal direction (e.g., along longitudinal line L of FIG. 5) of the heat transfer device to reduce the energy loss caused by change in direction of velocity. Heat loss will be increased as the change of velocity direction needs extra energy. The inlet and outlet are placed proximate to each other at the center of the bottom line in Area I. This is advantageous as the liquid will transport a relatively long route within the heat transfer device such that heat exchange between the liquid and the animate body can be more efficiently exploited. The flow velocity at the inlet is very high and centralized near the inlet. The turbulence kinetic energy will be high if too many barriers are placed at the entrance. The function of the points (i.e., dot connections and line connections) in Area I mainly acts for the decen-

TABLE 1

| | Parameters of materials used for fabrication of the heat transfer device according to certain embodiments | | | | | | |
|---|---|---|---|---|---|---|---|
| Materials | Weight g/m² | Thickness mm | Fabric | Yarn counts D | Warp/weft yarn density threads/inch | Polymer | Thickness mm |
| Inner layer | 251 | 0.25 | Nylon | 70 | 127/81 | TAF | 0.15 |
| Middle layer | 220 | 0.2 | — | — | — | TAF | 0.2 |
| Outer layer | 331 | 0.35 | Polyester | 300 | 53/48 | TAF | 0.1 |

Compared to the other layers, a larger heat flux for the inner layer is advantageous as it can enhance the heat transfer between the skin and the circulated liquid within the heat transfer device. The parameters in Table 2 are advantageous as they result in improved heat transfer performance, such as fast and uniform temperature distribution, efficient heat exchange, etc.

TABLE 2

| The heat transfer performance of inner and outer layers | | |
|---|---|---|
| Fabric | Thickness mm | Heat flux W/cm² |
| Inner TAF laminated fabric | 0.09-0.25 | 0.15-0.20 |
| Outer TAF laminated fabric | 0.35-0.50 | 0.05-0.13 |

Figure 7:
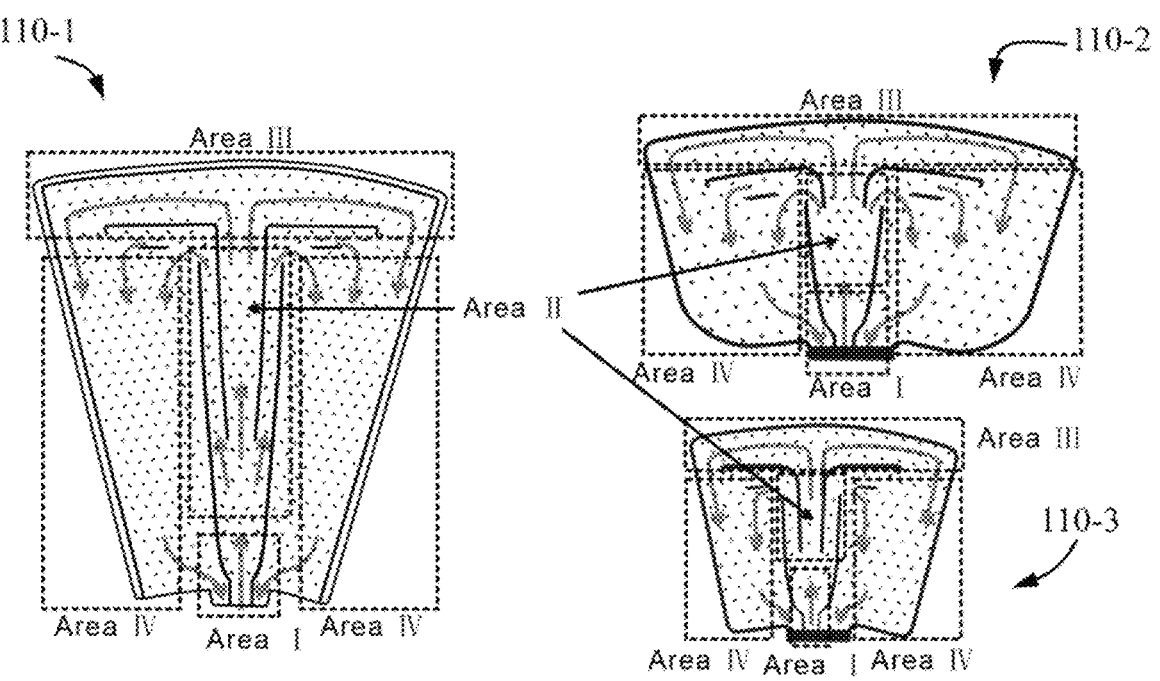
FIG. 7 illustrates flowing of liquid within three heat transfer devices appliable to a human's leg, thigh, and calf respectively according to certain embodiments of the present disclosure.

FIG. 7 illustrates liquid flowing routes within three heat transfer devices 110-1, 110-2 and 110-3 that are applied to a human's leg (left), thigh (upper right), and calf (bottom right) respectively.

Each heat transfer device comprises an active area or region, which may also be called a functional area. The active area refers to the area where the liquid conduit, the line connections and the dot connections are disposed and where most heat carried by liquid distributes within the heat transfer device. The active area can be divided into a first area (Area I, also called a decentralization area), a second area (Area II, also called a fast transfer area), a third area tralization of liquid flow. The dot connections in Area I can be scattered and the area will be inflated to increase the hydraulic radius to reduce the flow resistance. As the velocity is still very high after the decentralization, the function of Area II is to fast transfer the liquid from Area I to the top part of the heat transfer device. The dot connections in Area II can be arranged in a line for purpose of reducing flow resistance and avoiding too much inflation. In Area III, the flow velocity has been reduced and this area will also cause large quantities of kinetic energy loss due to the significant change in velocity vector. Two branches of Area III are designed to further decentralize the flow velocity. When the liquid comes to the main function area (i.e. Area IV), the density of the dot connections increases to decrease the consumption of liquid. In some embodiments, all the dot connections are configured in regular hexagonal arrangement (that is, each dot connection has a regular hexagonal shape). This benefits the distribution of the flow velocity. As a result, the flow velocity can distribute homogeneously in Area IV. This design leads to an improved flow rate and surface velocity uniformity.

Figure 8:
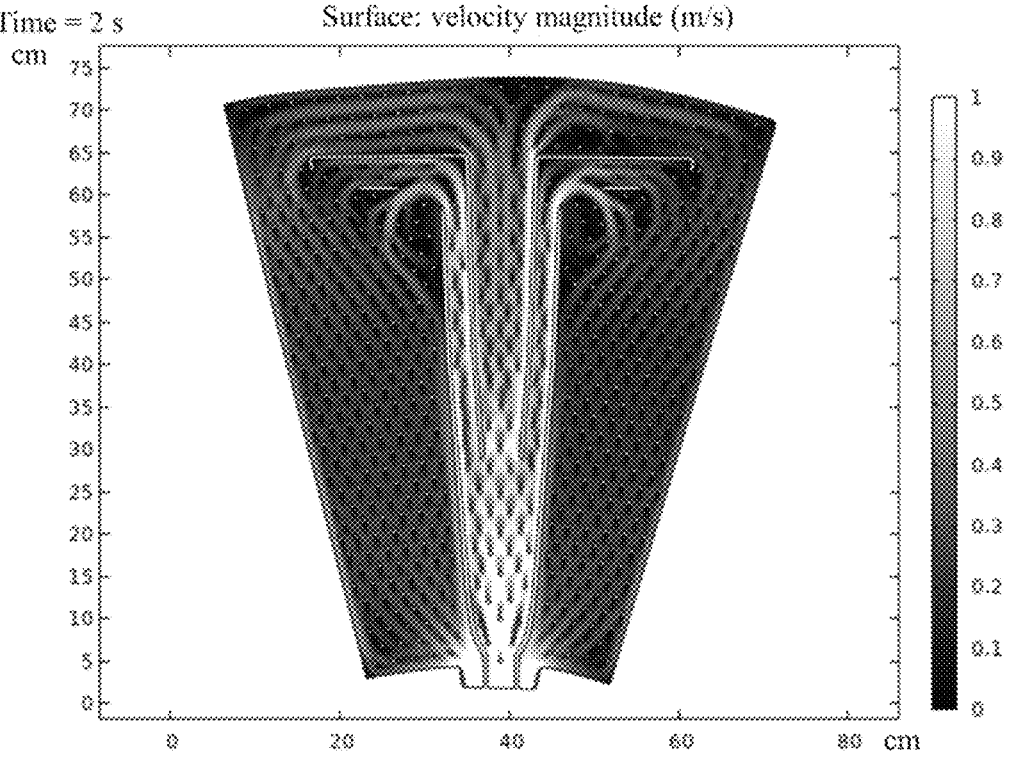
FIG. 8 illustrates a numerally simulated velocity distribution for liquid flowing within a heat transfer device according to certain embodiments of the present disclosure.

FIG. 8 shows a numerally simulated surface velocity distribution for liquid flowing in a heat transfer device. The heat transfer device has a same shape and configuration of the heat transfer device 110-1 of FIG. 7. The commercial software COMSOL Multiphysics 6.1 is used to conduct the simulation and the liquid is water. The two-dimensional (2D) geometrical parameters used are shown in FIG. 8. The velocity at the inlet is set as 1 m/s.

The simulation is conducted for a 2D structure, and the surface velocity in the simulation represents the velocity distribution in the middle part of the three-dimensional (3D) structure panel. The middle part may be considered as a cross section passing through the middle portion (such as the longitudinal line L in FIG. 5) of the heat transfer device. As can be seen, the velocity near the surface of the device is close to 0 m/s due to factors such as effect of boundary layer and nature of fluid viscosity. With the appropriate guiding line and dot connections, a highly uniform distribution of velocity in Area I is achieved. The flow drag is also desirably manipulated in Area II and III, so that the evenness can be enhanced in Area IV.

Figure 9:
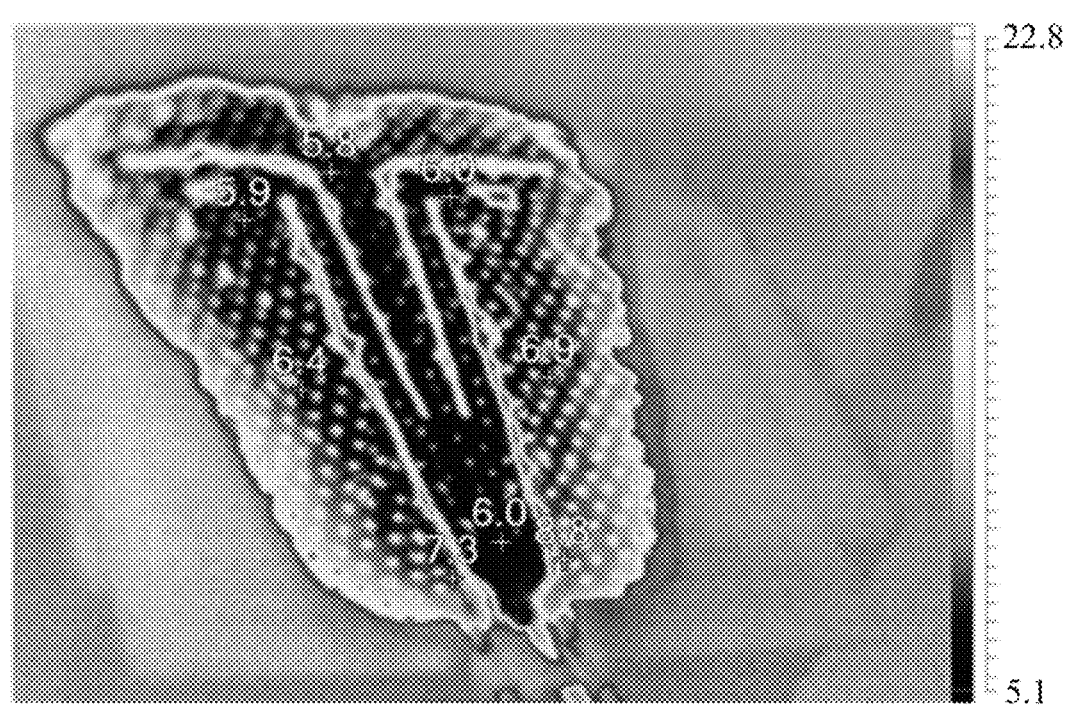
FIG. 9 illustrates a measured temperature distribution within a heat transfer device prototype according to certain embodiments of the present disclosure.
Figure 9:
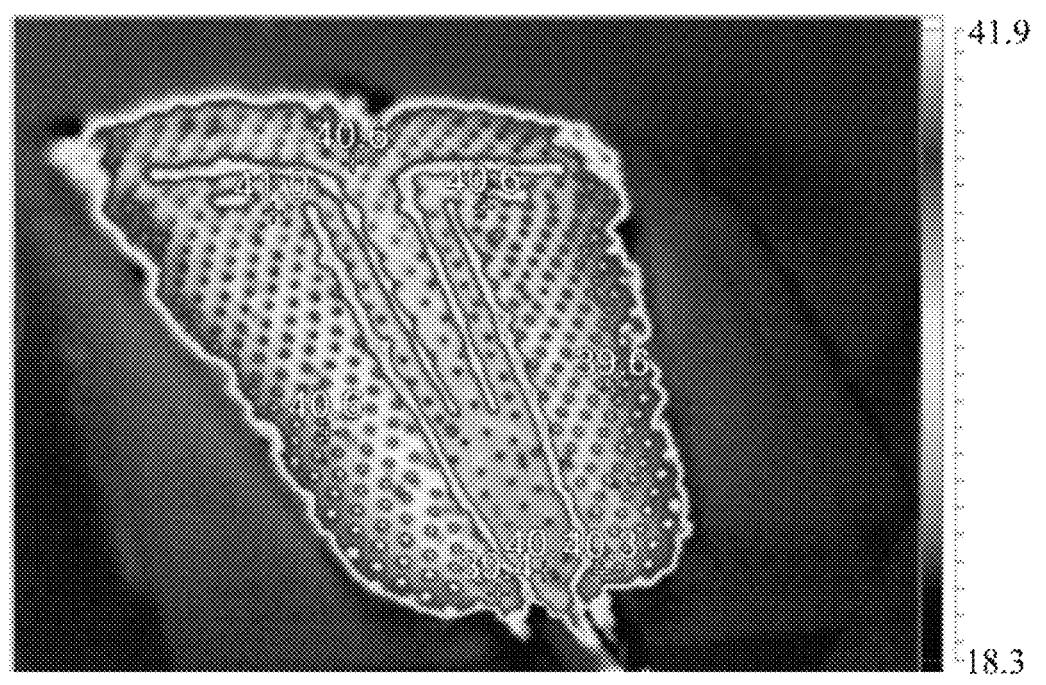

FIG. 9 shows a measured temperature distribution for a heat transfer device prototype. The prototype has a same shape and configuration of the heat transfer device 110-1 of FIG. 7. The measure is conducted when the heat transfer device is laid flat. The liquid is water (cold water and hot water) and the flow rate for the water at the inlet is around 4.1 L/min. A Fluke Ti400 Thermal Imager is used to take infrared video for the liquid flowing within the heat transfer device for obtaining the temperature data, which show the temperature distribution and change. The upper figure of FIG. 9 shows the temperature distribution of cold water, while the lower figure shows the temperature distribution of the hot water. It can be seen a uniform distribution of temperature is obtained within the heat transfer device. According to one or more embodiments, the uniform distribution of temperature can be achieved in a short time, as short as 10 s for example. This is advantageous over the existing systems where even filling of liquid (such as water) generally takes over 1 minute and more time is needed for a relatively uniform temperature distribution.

Figure 10:
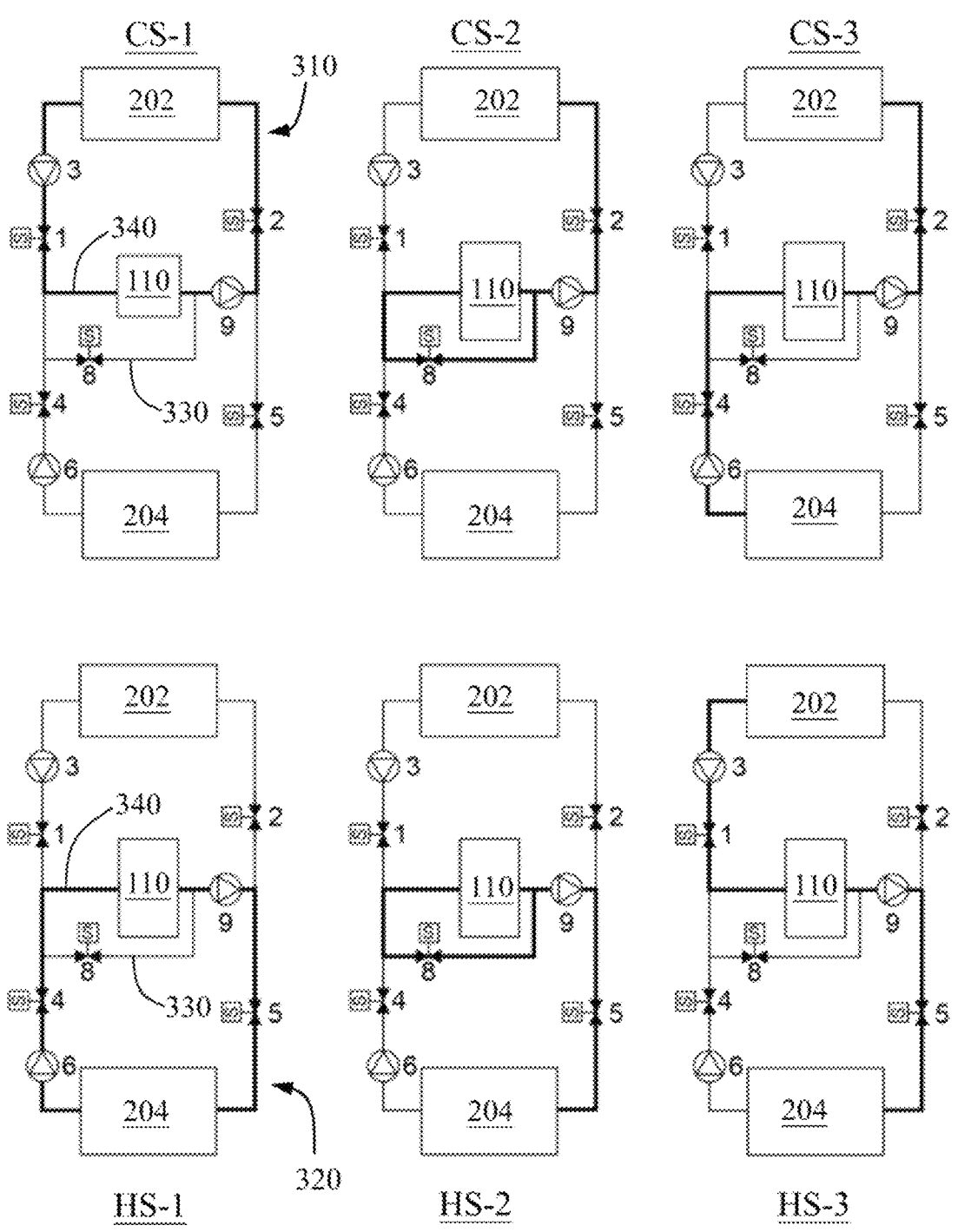
FIG. 10 illustrates first and second circulation loops and various stages of liquid circulation within a heat transfer system according to certain embodiments of the present disclosure.

FIG. 10 illustrates a first circulation loop 310 and a second circulation loop 320 and various stages or states CS-1, CS-2, CS-3, HS-1, HS-2, and HS-3 of liquid circulation within a heat transfer system.

For purpose of description, the first liquid source 202 is a cold tank for receiving a mixture of water and ice as a coolant. The second liquid source 204 is a hot tank for receiving hot water. The second liquid source 204 may be heated by heaters such that the water therein reaches a predetermined or desirable temperature, such as 30° C., 35° C., 40° C. or 45° C. The temperatures of water may be sensed by temperature sensors, such as thermocouples. There may be thermal feedback loop to stabilize the water temperature.

The six states or stage as shown are below: CS-1: cold cycle state; CS-2: cold drain state; CS-3: cold water reflux; HS-1: hot cycle state; HS-2: hot drain state; and HS-3: hot water reflux. Each state is a representative of a stage or configuration of a liquid transportation route. The bolded lines for each state indicate respective liquid transport route.

At stage CS-1, the first circulation loop 310 is established such that cold water transports to the heat transfer device 110 and flows therein to exchange heat with the animate body, and then returns to the first liquid source 202. The first circulation loop 310 comprises valves 1 and 2 (i.e., a first plurality of valves, such as solenoid valves), a pump 3 (i.e., a first pump) and a common pump 9. The common pump 9 may be a vacuum suction pump, which, for example, helps increase water flow rate when in water cycling and drain the water out when in drainage state.

At stage HS-1, the second circulation loop 320 is established such that hot water transports to the heat transfer device 110 and flows therein to exchange heat with the animate body, and then returns to the second liquid source 204. The second circulation loop 320 comprises valves 4 and 5 (i.e., a second plurality of valves, such as solenoid valves), a pump 6 (i.e., a second pump) and the common pump 9.

The first circulation loop 310 and the second circulation loop 320 share a common branch 340 where the heat transfer device 110 and the common pump 9 are disposed. The various valves can be pre-programmed to be closed (to disallow liquid to pass) or opened (to allow the liquid to pass) to reduce or avoid hot and cold water mixing. Therefore, the first and second liquid sources 202, 204 can separately and independently provide respective liquid, thereby to apply varying temperature to the animate body.

The other states, i.e., CS-2, CS-3, HS-2, and HS-3 are representatives of intermediary states in relation to switching between CS-1 and HS-1. A fast switching between CS-1 and HS-1 will improve the performance, such as effectiveness, of the heat transfer system for RCT. As further noted, a branch 330 is provided with one end connectable to the inlet of the heat transfer device 110 and with the other end connectable to the outlet of the heat transfer device 110. The branch 330 comprises a valve 8 (i.e., a third valve, such as solenoid valve). The valve 8 can be controlled to open (to allow liquid to pass) or close (to disallow liquid to pass) the branch 330. As described later below, the branch 330 facilitates draining of the first liquid (such as cold water) from the heat transfer device 110 into the first liquid source 202 when the liquid conduit is switched from the first circulation loop 310 to the second circulation loop 320, and facilitates draining of the second liquid (such as hot water) from the heat transfer device 110 into the second liquid source 204 when the liquid conduit is switched from the second circulation loop 320 to the first circulation loop 310.

By way of example, at stage CS-2, the valve 1 is closed and extraction of the cold water from the first liquid source 202 stops. In the meanwhile, the valve 2 continues to be opened, and the valve 8 is opened to complete the branch 330 such that the residual or leftover cold water in the heat transfer device 110 starts to be drained out and return to the first liquid source 202 through the branch 330, the common pump 9 and the valve 2.

Stage CS-3 shows a water reflux process. The valve 4 is opened and the pump 6 turns on, and thus the hot cycle starts. The valve 8 is closed to cut off the branch 330. But in the initial few seconds, the water discharged is still the cold water leftover from the previous cold cycle, which will be returned to the first liquid source 202 through the common pump 9 and the valve 2. After that, stage HS-1 starts to transport hot water with the valve 2 closed and the valve 5 opened.

It is desirable to drain all the cold water as quickly as possible to shorten the switching time of the system from the cold water circle to the hot water circle. However, generally at stage CS-2 not all cold water can be drained out of the heat transfer device 110 as this process takes time. The water reflux process at stage CS-3 solves this problem by quickly draining the remaining cold water from the heat transfer device 110 and returning this cold water to the first liquid source 202. As a result, this shortens the drainage time and decreases cold water and hot water mixing, which also reduces energy waste.

At stage HS-2, the valve 4 is closed and extraction of the hot water from the second liquid source 204 stops. In the meanwhile, the valve 5 continues to be opened, and the valve 8 is opened to complete the branch 330 such that the residual or leftover hot water in the heat transfer device 110 starts to be drained out and return to the second liquid source 204 through the branch 330, the common pump 9 and the valve 5.

Stage HS-3 shows a water reflux process. The valve 1 is opened and the pump 3 turns on, and thus the cold cycle starts. The valve 8 is closed to cut off the branch 330. But in the initial few seconds, the water discharged is still the hot water left over from the previous hot cycle, which will be returned to the second liquid source 204 through the common pump 9 and the valve 5. After that, stage CS-1 starts to transport cold water with the valve 5 closed and the valve 2 opened.

It is desirable to drain all the hot water as quickly as possible to shorten the switching time of the system from the hot water circle to the cold water circle. However, generally at stage HS-2 not all hot water can be drained out of the heat transfer device 110 as this process takes time. The water reflux process at stage HS-3 solves this problem by quickly draining the remaining hot water from the heat transfer device 110 and returning this hot water to the second liquid source 204. As a result, this shortens the drainage time and decreases hot water and cold water mixing, which also reduces energy waste.

The switch logics can be set according to practical needs, such as size and number of the heat transfer devices, the requirements for specific applications, etc. The switch logics, such as opened/closed state of the valves, ON/OFF of the pumps, etc. may be controlled by a controller.

Figure 11:
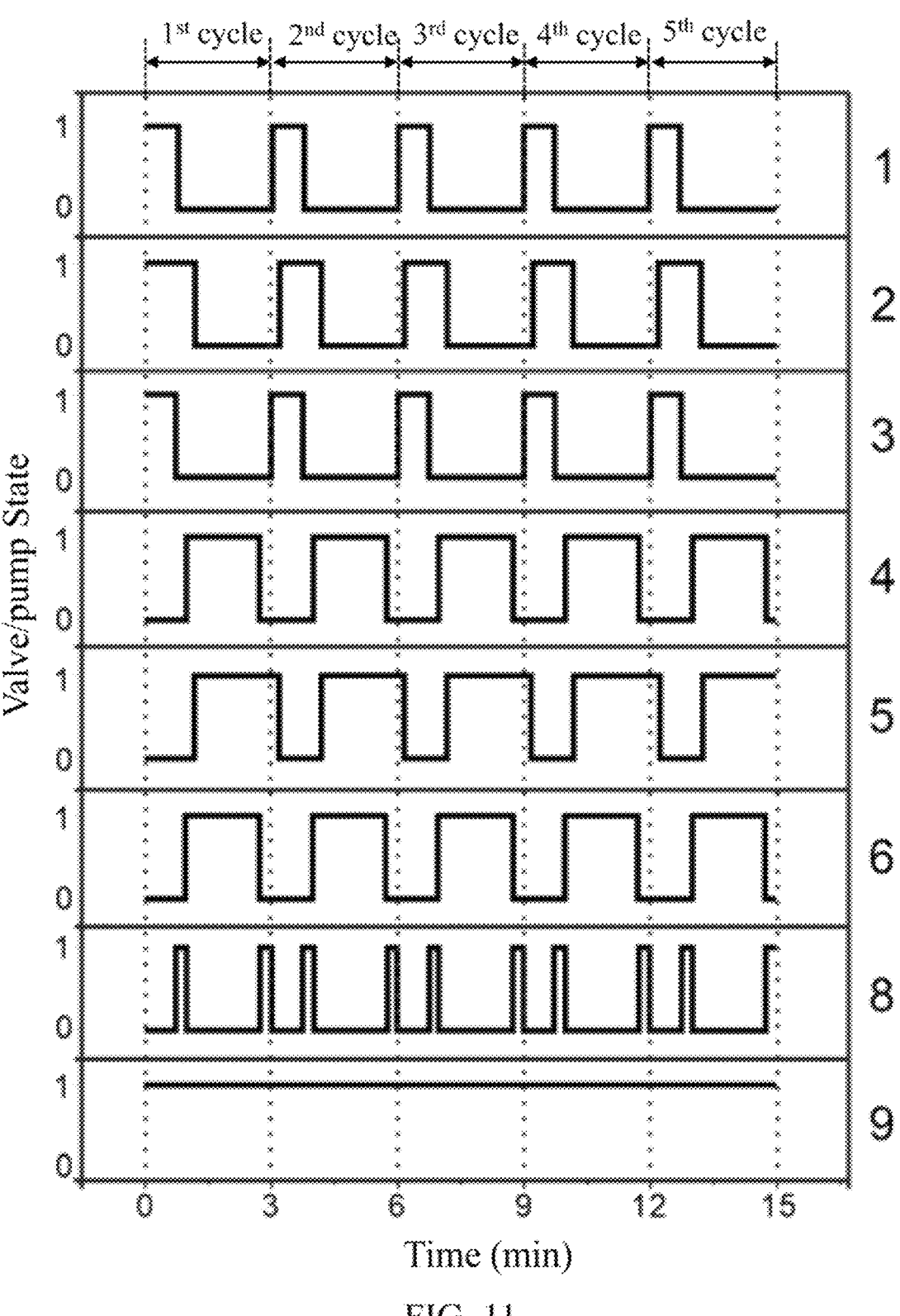
FIG. 11 illustrates control logic for the pumps and valves of FIG. 10 according to certain embodiments of the present disclosure.

A PLC may be programmed to set the time-series of the switch logic for the flow control of hot and cold fluids via pumps and valves at predetermined time intervals. FIG. 11 shows a control logic for the pumps and valves of FIG. 10. The control logic comprises five cycles, where the number "0" on the left vertical coordinate means the state of the valve is closed or the pump is at OFF state such that the fluid cannot pass through the valve/pump, while the number "1" on the left vertical coordinate means the valve is opened or the pump is at ON state such that the fluid can pass the valve/pump. The numbers from 1 to 9 on the right vertical coordinate are reference numerals for pumps and valves in FIG. 10. The first cycle and the following four cycles are different as the first cycle does not need water reflux. The following four cycles share the same time shift logics as shown in FIG. 11 and Table 3.

TABLE 3

| Example of one time shift details specially for whole leg | | |
|---|---|---|
| | State of cycle | Time of duration(s) |
| 1st cold | Cold cycle | 45 |
| drain | Cold drain | 15 |
| 1st hot + drain | Cold water reflux procedure | 11 |
| 1st hot | Hot cycle | 94 |
| drain | Hot drain | 15 |
| 2nd cold + drain | Hot water reflux procedure | 11 |
| 2nd cold | Cold cycle | 34 |
| drain | Cold drain | 15 |
| 2nd hot + drain | Cold water reflux procedure | 11 |
| 2nd hot | Hot cycle | 94 |
| drain | Hot drain | 15 |

In Table 3, the word "hot+drain" means in the hot cycle, but at the beginning of the first 11 s, the cold water left in the heat transfer device is drained and returns to the cold tank. This process corresponds to the stage CS-3. The word "cold+drain" means in the cold cycle, but at the beginning of the first 11 s, the hot water left in the heat transfer device is drained and returns to the hot tank. This process corresponds to the stage HS-3.

Figure 12A:
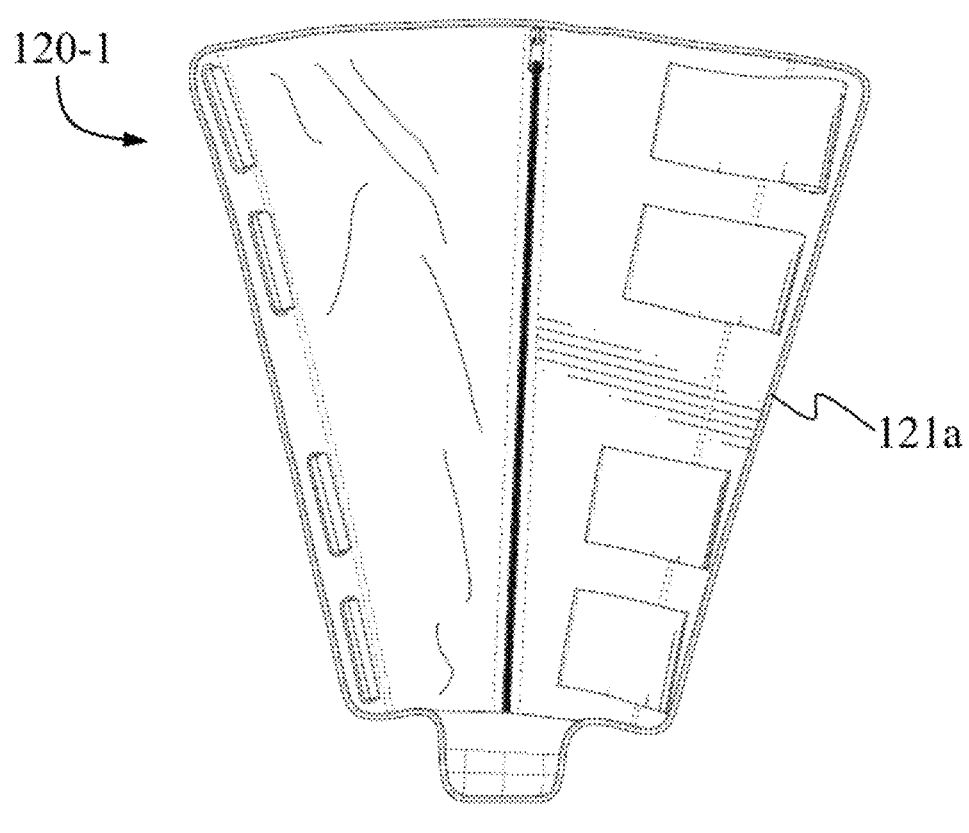
FIG. 12A illustrates ergonomic body pieces used for a leg according to certain embodiments of the present disclosure.
Figure 12A:
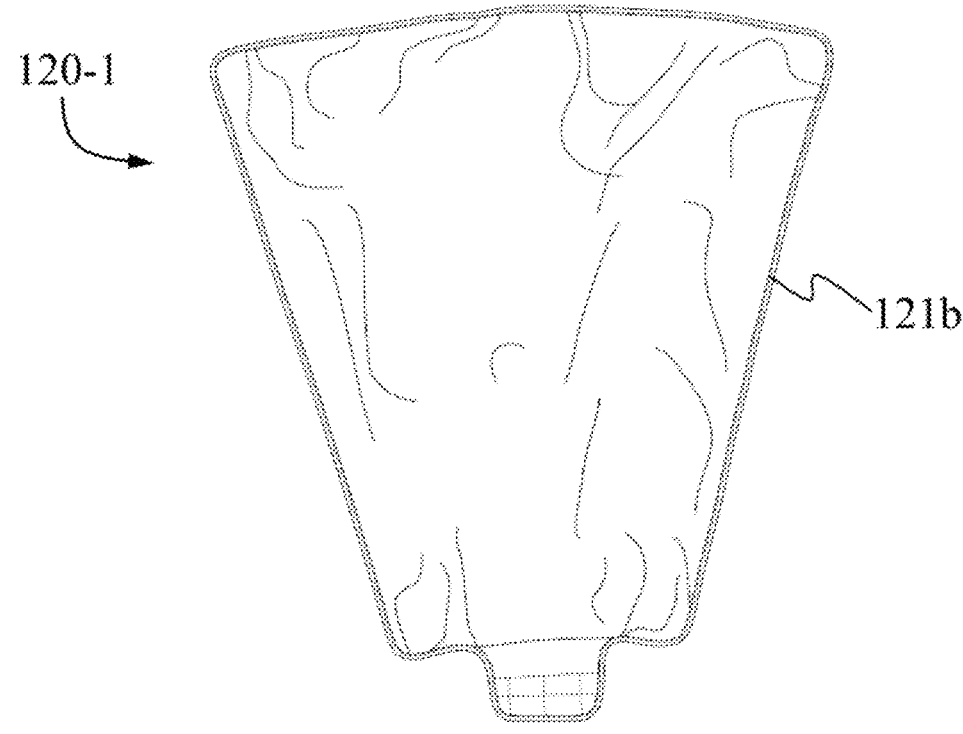

FIG. 12A illustrates ergonomic body pieces 120-1 used for a human's leg. The ergonomic body pieces 120-1 comprise a first cover 121a and a second cover 121b that together define an inner space for receiving the heat transfer device 110. The first cover 121a may be made of nylon shell fabrics with thermoplastic polyurethane (TPU) backing. The second cover 121b may be made of lightweight waterproof nylon lining fabric. In operation the second cover 121b contacts the leg.

Figure 12B:
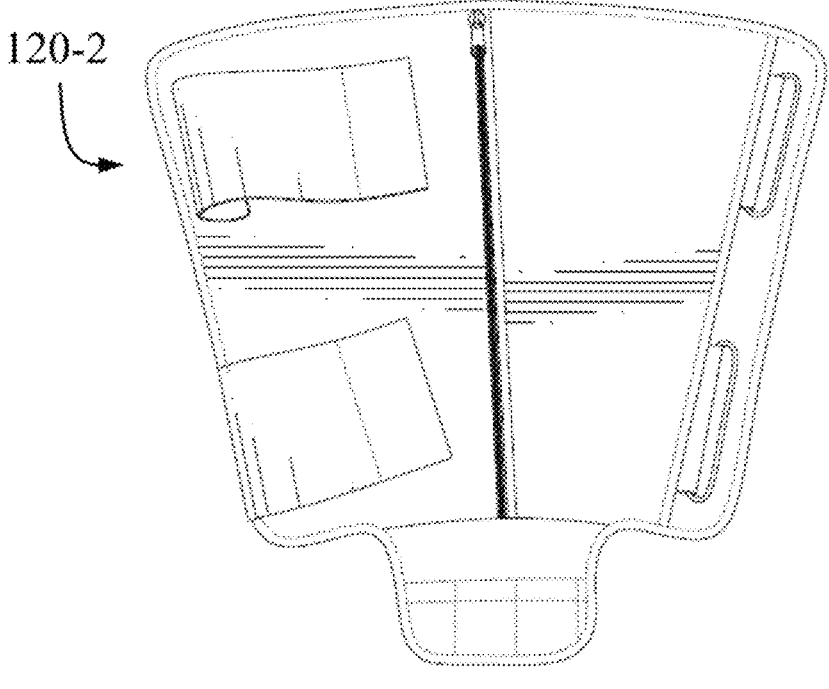
FIG. 12B illustrates ergonomic body pieces used for a calf according to certain embodiments of the present disclosure.
Figure 12C:
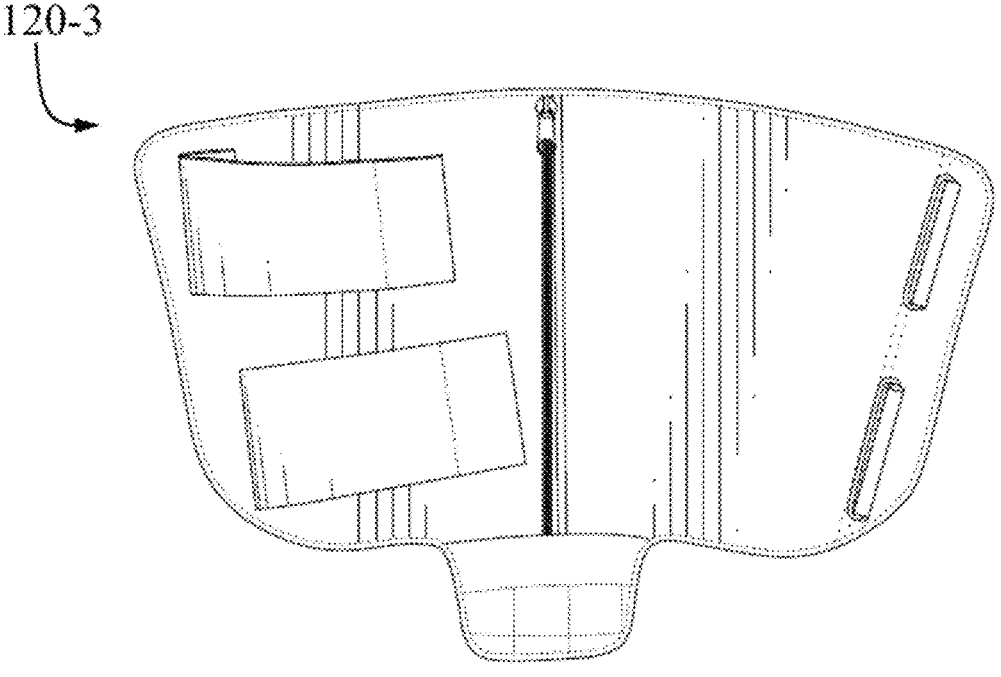
FIG. 12C illustrates ergonomic body pieces used for a thigh according to certain embodiments of the present disclosure.

FIGS. 12B and 12C illustrates ergonomic body pieces 120-2, 120-3 used for a calf and a thigh respectively. The ergonomic body pieces 120-2, 120-3 have similar shape as that of the ergonomic body pieces 120-1, but different size as they are used for different portion of the human body. They are adapted so as to be complaint to the specific portion of the animate body to be applied.

FIGS. 13A, 13B, 13C, and 13D illustrate how the heat transfer device 110 is inserted and received into the ergonomic body pieces 120 and then how the ergonomic body pieces 120 are wrapped onto a human's leg (the leg is not shown).

Figure 13A:
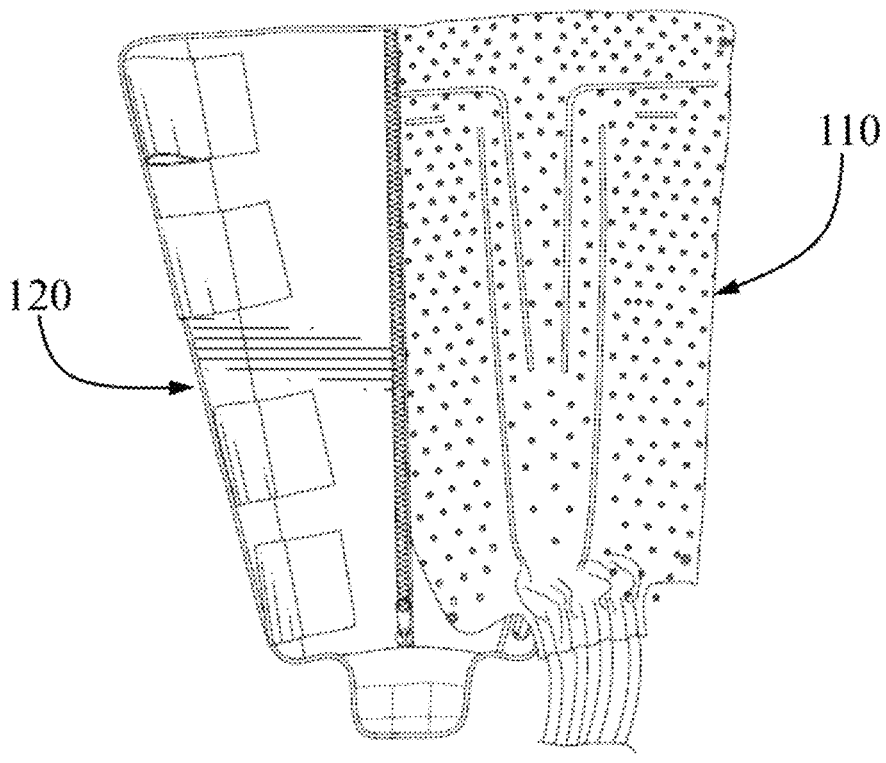
FIG. 13A illustrates a part of a heat transfer device has inserted into ergonomic body pieces according to certain embodiments of the present disclosure.
Figure 13B:
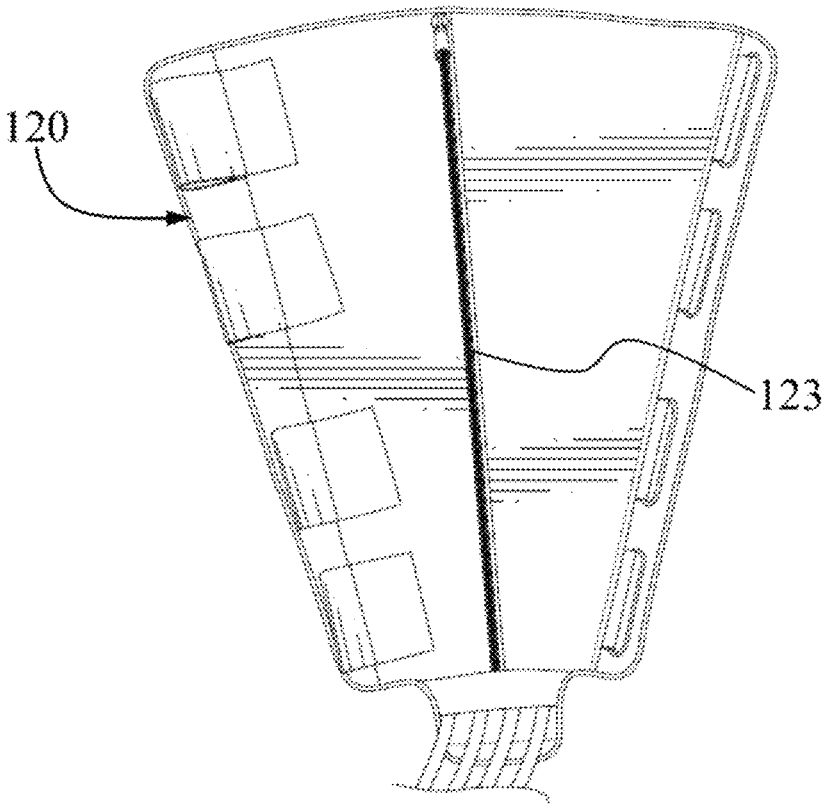
FIG. 13B illustrates the heat transfer device of FIG. 13A has fully received in the ergonomic body pieces.
Figure 13C:
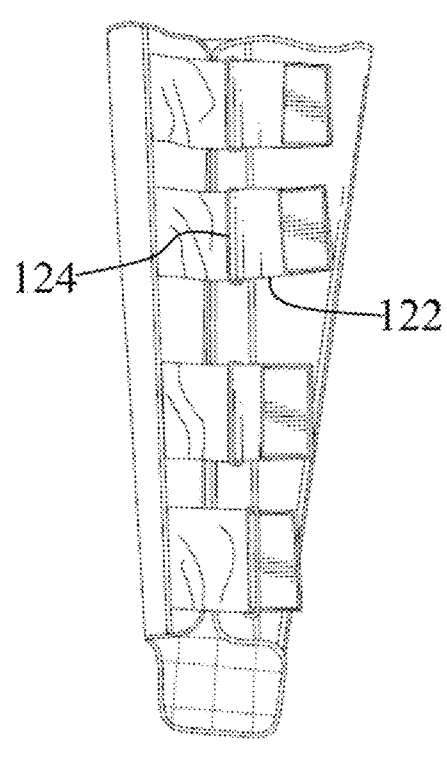
FIG. 13C illustrates the ergonomic body pieces of FIG. 13B wrap around with the straps passing through the buckles.
Figure 13D:
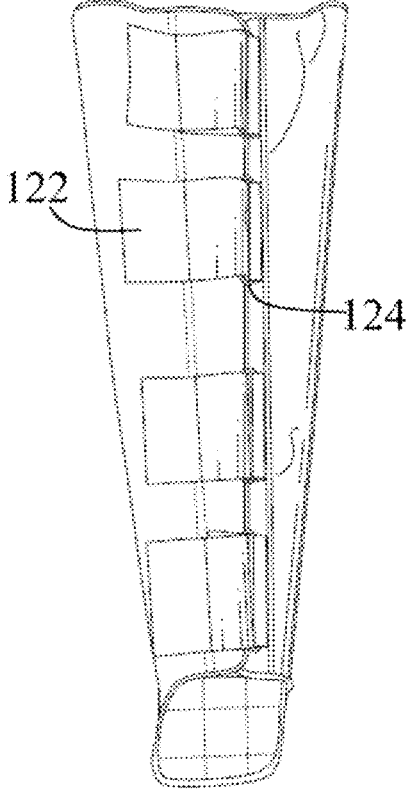
FIG. 13D illustrates the ergonomic body pieces of FIG. 13C are fixed.

In the present embodiment, to place the heat transfer device 110 into the ergonomic body pieces 120, the ergonomic body pieces120 is first opened by operating a zipper 123, such as pulling the zipper 123 in a first direction. Then the heat transfer device 110 is allowed to be inserted into the inner space of the ergonomic body pieces 120 from one side (FIG. 13A). After the heat transfer device 110 is fully inserted into the ergonomic body pieces 120, the ergonomic body pieces 120 can be sealed by pulling the zipper 123 in a second direction opposite the first direction (FIG. 13B). Then the ergonomic body pieces 120 is wrapped onto the leg such that each strap 122 on one border passes through a respective buckle 124 on the opposite border (FIG. 13C). The open end of each strap 122 has adhesive tab that can be used to fix the strap 122 onto the buckle 124 (FIG. 13D).

As used herein, the term "connect", "connectable" and the like in relation to two elements means the two elements are connected physically, or electrically, or both, directly or indirectly through one or more intermediaries.

As used herein, the term "varying temperature" means the temperature does not always remain the same. The temperature can vary constantly, or can remain for a certain period of time, and then change to a different value.

As used herein, the terms "high temperature" and "low temperature" are referenced relative to each other and merely mean the two temperatures are different. That is, the high temperature is higher than the low temperature, and the low temperature is lower than the high temperature. Further, the high temperature is associated with the temperature of the liquid in the second liquid source, and the low temperature is associated with the temperature of the liquid in the first liquid source.

As used herein, the terms "hot" and "cold" are referenced relative to each other and merely mean two items carrying different temperatures. For example, the hot water means the water temperature is higher than that of cold water.

It will further be appreciated that any of the features in the above embodiments of the invention may be combined together and are not necessarily applied in isolation from each other. Similar combinations of two or more features from the above-described embodiments or preferred forms of the invention can be readily made by one skilled in the art.

Unless otherwise defined, the technical and scientific terms used herein have the plain meanings as commonly understood by those skill in the art to which the example embodiments pertain. Embodiments are illustrated in non-limiting examples. Based on the above disclosed embodiments, various modifications that can be conceived of by those skilled in the art would fall within spirits of the example embodiments.

What is claimed is:

1. A heat transfer device for applying a varying temperature to a portion of an animate body, the heat transfer device comprising a liquid conduit, the liquid conduit being liquidly connectable to an external first liquid source to establish a first circulation loop for transporting a first liquid, the liquid conduit being liquidly connectable to an external second liquid source to establish a second circulation loop for transporting a second liquid, the second liquid having a higher temperature than the first liquid, wherein the liquid conduit is operably switchable between the first circulation loop and the second circulation loop for achieving the varying temperature applied to the portion of the animate body, wherein the heat transfer device further comprises:

a first layer and a second layer that form the liquid conduit for allowing liquid to flow therein, the liquid being the first liquid or the second liquid or both, wherein the first layer is operably disposed closer to the portion of the animate body than the second layer, line connections and dot connections for coupling the first layer and the second layer, thereby to modify the liquid conduit, wherein the density of the dot connections is non-uniform, and a first area, a second area, a third area, and a fourth area such that substantial proportion of liquid flow subsequently through the first area, the second area, the third area, and the fourth area, wherein the dot connections of the fourth area have larger density than the dot connections in the first area, wherein the liquid conduit comprises an inlet and two outlets, the inlet and the two outlets being disposed in the first area, wherein the third area comprises:

a first branch for directing liquid to one of the two outlets via a first portion of the fourth area; and a second branch for directing liquid to the other one of the two outlets via a second portion of the fourth area.

2. The heat transfer device of claim 1, wherein each of the dot connections has a regular hexagonal shape.

3. The heat transfer device of claim 1, wherein the first layer has a smaller hardness than the second layer.

4. The heat transfer device of claim 1, wherein the first layer is configured to achieve a larger heat flux than the second layer.

5. The heat transfer device of claim 4, wherein the heat flux achievable by the first layer is in a range from 0.15 W/cm$^2$ to 0.20 W/cm$^2$, and the heat flux achievable by the second layer is in a range from 0.05 W/cm$^2$ to 0.13 W/cm$^2$.

6. The heat transfer device of claim 1, wherein the first layer comprises thermoplastic adhesive film-laminated fabric, and the second layer comprises a thermoplastic adhesive film or double thermoplastic adhesive film-laminated fabrics.

7. The heat transfer device of claim 1, further comprising a third layer such that the second layer is disposed between the first layer and the third layer, the second layer and the third layer defining a gas conduit for receiving pressured gas for applying compression to the portion of the animate body.

8. A heat transfer system comprising:

a wearable apparatus configured to be wearable onto a portion of an animate body for applying a varying temperature to the portion of the animate body, the wearable apparatus comprising a heat transfer device; and a portable apparatus connectable to the wearable apparatus for supplying liquid with the varying temperature to the wearable apparatus, the portable apparatus comprising a first liquid source, a second liquid source, and a control unit, wherein the heat transfer device comprises a liquid conduit, the liquid conduit being liquidly connectable to the first liquid source to establish a first circulation loop for carrying a first liquid, the liquid conduit being liquidly connectable to the second liquid source to establish a second circulation loop for carrying a second liquid, the second liquid has a higher temperature than the first liquid, wherein the control unit is configured to switch connection of the liquid conduit between the first circulation loop and the second circulation loop for achieving the varying temperature applied to the portion of the animate body, wherein the heat transfer device further comprises:

a first layer and a second layer that form the liquid conduit for allowing liquid to flow therein, the liquid being the first liquid or the second liquid or both, wherein the first layer is operably disposed closer to the portion of the animate body than the second layer, line connections and dot connections for coupling the first layer and the second layer, thereby to modify the liquid conduit, wherein the density of the dot connections is non-uniform, and a first area, a second area, a third area, and a fourth area such that substantial proportion of liquid flow subsequently through the first area, the second area, the third area, and the fourth area, wherein the dot connections of the fourth area have larger density than the dot connections in the first area, wherein the liquid conduit comprises an inlet and two outlets, the inlet and the two outlets being disposed in the first area, wherein the third area comprises:

a first branch for directing liquid to one of the two outlets via a first portion of the fourth area; and a second branch for directing liquid to the other one of the two outlets via a second portion of the fourth area.

9. The heat transfer system of claim 8, wherein the first liquid is a mixture of water and coolant, and the second liquid is heated water.

10. The heat transfer system of claim 8, wherein the first circulation loop comprises the heat transfer device, the first liquid source, a first pump, a common pump, and a first plurality of valves, wherein the second circulation loop comprises the heat transfer device, the second liquid source, a second pump, the common pump, and a second plurality of valves, wherein the heat transfer system further comprises a branch and a third valve disposed in the branch, one end of the branch being connectable to the inlet and the other end of the branch being connectable to the outlets, wherein the branch is configured to facilitate draining of the first liquid from the heat transfer device into the first liquid source when the liquid conduit is switched from the first circulation loop to the second circulation loop, or to facilitate draining of the second liquid from the heat transfer device into the second liquid source when the liquid conduit is switched from the second circulation loop to the first circulation loop.

11. The heat transfer system of claim 10, wherein the control unit comprises a programmable logic controller configured to be programable to control opening or closing of the first circulation loop, the second circulation loop, and the third valve.

12. The heat transfer system of claim 8, wherein the wearable apparatus comprises tubes for connecting the heat transfer device to the portable apparatus, and each of the tubes is covered with an insulating material and a protective sleeve.

13. The heat transfer system of claim 8, wherein the wearable apparatus comprises ergonomic body pieces for carrying the heat transfer device, and the ergonomic body pieces comprise fixtures configured to fix the ergonomic body pieces onto the portion of the animate body when the ergonomic body pieces wrap onto the portion of the animate body.

14. The heat transfer system of claim 13, wherein the fixtures comprise a plurality of buckles and a plurality of straps, each strap being fixable to a corresponding buckle.

15. The heat transfer system of claim 8, wherein the portable apparatus comprises a power source, the power source comprising one or more batteries for supplying power to the heat transfer system.

16. The heat transfer system of claim 8, wherein the heat transfer device comprises a gas conduit, and the portable apparatus comprises a pneumatic module for providing pressured gas to the gas conduit for applying compression to the port of the animate body.

* * * * *